United States Patent
Tang et al.

(10) Patent No.: US 12,404,506 B2
(45) Date of Patent: Sep. 2, 2025

(54) SPLINT NUCLEIC ACID MOLECULE FOR CYCLIZING SINGLE-STRANDED NUCLEIC ACID MOLECULE AND USE THEREOF

(71) Applicant: BGI GENOMICS CO., LTD., Guangdong (CN)

(72) Inventors: Chong Tang, Guangdong (CN); Juan Wang, Guangdong (CN); Yiqin Tong, Guangdong (CN); Linfeng Yang, Guangdong (CN); Qiang Gao, Guangdong (CN)

(73) Assignee: BGI GENOMICS CO., LTD., Guangdong (CN)

( * ) Notice: Subject to any disclaimer, the term of this patent is extended or adjusted under 35 U.S.C. 154(b) by 1367 days.

(21) Appl. No.: 17/043,447

(22) PCT Filed: Apr. 28, 2018

(86) PCT No.: PCT/CN2018/085086
§ 371 (c)(1),
(2) Date: Sep. 29, 2020

(87) PCT Pub. No.: WO2019/205135
PCT Pub. Date: Oct. 31, 2019

(65) Prior Publication Data
US 2021/0024933 A1    Jan. 28, 2021

(51) Int. Cl.
*C12Q 1/6806* (2018.01)
*C12N 15/113* (2010.01)
*C12Q 1/6851* (2018.01)

(52) U.S. Cl.
CPC .......... *C12N 15/113* (2013.01); *C12Q 1/6806* (2013.01); *C12Q 1/6851* (2013.01); *C12Q 2521/501* (2013.01); *C12Q 2525/191* (2013.01); *C12Q 2525/204* (2013.01); *C12Q 2527/101* (2013.01); *C12Q 2527/107* (2013.01); *C12Q 2527/113* (2013.01); *C12Q 2533/107* (2013.01)

(58) Field of Classification Search
CPC ............ C12Q 1/6806; C12Q 2521/501; C12Q 2525/191; C12Q 2525/204; C12Q 2527/101; C12Q 2527/113; C12Q 2533/107; C12Q 1/686
See application file for complete search history.

(56) References Cited

U.S. PATENT DOCUMENTS

| | | | | |
|---|---|---|---|---|
| 7,700,323 B2 * | 4/2010 | Willis | ................... | C12Q 1/6827 435/6.12 |
| 11,485,966 B2 * | 11/2022 | Wang | ................... | C12Q 1/6869 |
| 2003/0232348 A1 * | 12/2003 | Jones | ................... | C12Q 1/6809 435/6.12 |
| 2008/0199916 A1 * | 8/2008 | Zheng | ................... | C12Q 1/6844 435/91.2 |

FOREIGN PATENT DOCUMENTS

| | | | |
|---|---|---|---|
| CN | 105986324 A | 10/2016 | |
| CN | 109652499 A * | 4/2019 | ............... C12Q 1/34 |
| EP | 1196630 A2 | 4/2002 | |
| WO | WO-2019071471 A1 * | 4/2019 | ......... C12N 15/1006 |

OTHER PUBLICATIONS

Machine translation of CN 109652499 A (Year: 2019).*
Qi et al. L-RCA (ligation-rolling circle amplification): a general method for genotyping of single nucleotide polymorphisms (SNPs). Nucleic Acids Research 2001; 29: e116. (Year: 2001).*
Faruqi et al. High-throughput genotyping of single nucleotide polymorphisms with rolling circle amplification. BMC Genomics 2001; 2: 4 (Year: 2001).*
Szemes et al. Diagnostic application of padlock probes-multiplex detection of plant pathogens using universal microarrays. Nucleic Acids Research 2005; 33: e70 (Year: 2005).*
Zheng, Hongning "DNA and RNA Assembly Nanotechnology based on Small Circular DNA Molecules" China Doctoral Dissertations Full-Text Database (Basic Sciences) No. 3, Mar. 15, 2015, Abstract Only.
Villani, G., et al. "Gap-Directed Translesion DNA Synthesis of an Abasic Site on Circular DNA Templates by a Human Replication Complex" PLOS ONE, vol. 9, Apr. 7, 2014, pp. 1-8.
International Search Report issued for PCT/CN2018/085086, dated Jan. 24, 2019.
Written Opinion of the International Searching Authority issued for PCT/CN2018/085086, dated Jan. 24, 2019, with machine English translation.

* cited by examiner

*Primary Examiner* — Angela M. Bertagna
(74) *Attorney, Agent, or Firm* — Westman, Champlin & Koehler, P.A.; Z. Peter Sawicki; Amanda M. Prose

(57) ABSTRACT

Provided in the present invention are a splint nucleic acid molecule for cyclizing a single-stranded nucleic acid molecule and an application therefor. The splint nucleic acid, molecule is composed of a 5' terminal fragment and a 3' terminal fragment, the 5' terminal fragment being adapted to forming a first complementary region with a 5' terminal of the single-stranded nucleic acid molecule, and the 3' terminal fragment being suited to forming a second complementary region with a 3' terminal of the single-stranded nucleic acid molecule, the length of the first complementary region and the second complementary region being different.

14 Claims, 4 Drawing Sheets
Specification includes a Sequence Listing.

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial
<220> FEATURE:
<223> OTHER INFORMATION: nucleotide sequence of 5'terminal fragment of
      splint nucleic acid molecule

<400> SEQUENCE: 1
aagtcggatc gtagccatgt cgttc                                           25

<210> SEQ ID NO 2
<211> LENGTH: 11
<212> TYPE: DNA
<213> ORGANISM: Artificial
<220> FEATURE:
<223> OTHER INFORMATION: nucleotide sequence of 3'terminal fragment of
      splint nucleic acid molecule
```

```
<400> SEQUENCE: 2
tgtgagccaa g                                                             11

<210> SEQ ID NO 3
<211> LENGTH: 36
<212> TYPE: DNA
<213> ORGANISM: Artificial
<220> FEATURE:
<223> OTHER INFORMATION: nucleotide sequence of splint nucleic acid
      molecule

<400> SEQUENCE: 3
aagtcggatc gtagccatgt cgttctgtga gccaag                                  36
```

SPLINT NUCLEIC ACID MOLECULE FOR CYCLIZING SINGLE-STRANDED NUCLEIC ACID MOLECULE AND USE THEREOF

PRIORITY INFORMATION

This application is a Section 371 National Stage Application of International Application No. PCT/CN2018/085086, filed with the China National Intellectual Property Administration on Apr. 28, 2018, the entire content of which is incorporated herein by reference.

FIELD

The present disclosure relates to the field of biotechnology. Particularly, the present disclosure relates to a splint nucleic acid molecule for cyclizing a single-stranded nucleic acid molecule and the use thereof. More particularly, the present disclosure relates to a splint nucleic acid molecule for cyclizing a single-stranded nucleic acid molecule, a method for cyclizing a single-stranded nucleic acid molecule, a method for constructing a sequencing library, a sequencing library, a method for DNA sequence analysis, a kit, a device for cyclizing a single-stranded nucleic acid molecule, a system for constructing a sequencing library and a system for DNA sequence analysis.

BACKGROUND

BGISEQ-500 and MGI2000, as open platforms, provide a one-stop sequencing operation procedure with clarity, which not only include optional library construciton systems and sample loading systems, but also support a plurality of matching library construciton methods. The sequencing platforms as the leading high-throughput sequencing platforms in the field have adopted optimized combinatorial probe-anchor synthesis (cPAS) and improved DNA nanoball (DNB) core sequencing technology.

However, the existing library construction technology still needs to be developed and improved.

SUMMARY

The present disclosure is completed based on inventors' discovery of following facts and problems.

The library construction procedure based on the existing DNA nanoball (DNB) sequencing technology is characterized in that single-stranded nucleic acid molecules to be cyclized are self-ligated and cyclized when mediated by splint nucleic acid molecules and ligases and the cyclized single-stranded nucleic acid molecules are subjected to rolling circle amplification to form a DNB sequencing library. Apparently, the cyclization reaction is a very important part of the library construction procedure. During the in-depth study of influencing factors of cyclization reaction, the inventors found that the unproperly chosen splint nucleic acid molecule would result in low cyclization efficiency. Specifically, the single-stranded nucleic acid molecules to be cyclized cannot be totally self-ligated into circles, but a large amount of them generate linear complexes of the single-stranded nucleic acid molecules and the splint nucleic acid molecules or renatured double-stranded nucleic acid molecules (i.e., renatured double-stranded structure of the single-stranded nucleic acid molecule), which causes imbalance of positive and negative strands during sequencing and separation of adenine (A) and thymine (T) bases (or guanine (G) and cytosine (C) bases), thereby affecting the accuracy of DNA quantification and SNP determination.

The present disclosure aims to solve one of the technical problems in the related art at least to a certain extent. For this, the present disclosure in embodiments proposes a new splint nucleic acid molecule (i.e., splint oligo) and a new method for library construction based on the splint oligo. Use of the splint nucleic acid molecule according to the present disclosure can effectively improve the cyclization efficiency of single-stranded nucleic acid molecules.

In a first aspect, the present disclosure in embodiments provides a splint nucleic acid molecule for cyclizing a single-stranded nucleic acid molecule. In an embodiment, the splint nucleic acid molecule for cyclizing a single-stranded nucleic acid molecule consists of a 5' terminal fragment and a 3' terminal fragment, wherein the 5' terminal fragment is adapted to form a first complementary region between the 5' terminal fragment and a 5' terminal of the single-stranded nucleic acid molecule, the 3' terminal fragment is adapted to form a second complementary region between the 3' terminal fragment and a 3' terminal of the single-stranded nucleic acid molecule, and a length of the first complementary region is different from a length of the second complementary region. According to the embodiment, the first complementary region and the second complementary region can be formed via annealing at different temperatures because of the length difference between the first complementary region and the second complementary region, thereby effectively avoiding the intermolecular ligation of the single-stranded nucleic acid molecules to be cyclized and effectively improving the self-cyclization efficiency of the single-stranded nucleic acid molecules to be cyclized.

In a second aspect, the present disclosure in embodiments provides a method for cyclizing a single-stranded nucleic acid molecule. In an embodiment, the method for cyclizing a single-stranded nucleic acid molecule comprises allowing a reaction mixture containing the splint nucleic acid molecule described in the first aspect, the single-stranded nucleic acid molecule described in the first aspect and a ligase to be under a condition suitable for ligation, so as to obtain a cyclized single-stranded nucleic acid molecule. According to the embodiment, the first complementary region and the second complementary region can be formed via annealing at different temperatures because of the length difference between the first complementary region and the second complementary region as described above, thereby effectively avoiding the intermolecular ligation of the single-stranded nucleic acid molecules to be cyclized and effectively improving the self-cyclization efficiency of the single-stranded nucleic acid molecules to be cyclized. Specifically, it is possible to effectively avoid the formation of linear complexes of the single-stranded nucleic acid molecules and the splint nucleic acid molecules or renatured double-stranded nucleic acid molecules, thus significantly increasing the intramolecular self-ligation efficiency and self-cyclization efficiency of the single-stranded nucleic acid molecules compared to the prior art.

In a third aspect, the present disclosure in embodiments provides a method for constructing a sequencing library. In an embodiment, the method for constructing a sequencing library comprises subjecting a single-stranded nucleic acid molecule carrying an insert fragment to performing the method as described in the second aspect, thereby obtaining a product containing a cyclized single-stranded nucleic acid molecule carrying an insert fragment; and digesting the product containing a cyclized single-stranded nucleic acid molecule carrying an insert fragment, so as to obtain a cyclized sequencing library, wherein the single-stranded nucleic acid molecule carrying an insert fragment comprises an insert fragment, a first adaptor connected to a 5' terminal of the insert fragment, and a second adaptor connected to a 3' terminal of the insert fragment. According to the embodiment, it is possible to effectively avoid the formation of linear complexes of the single-stranded nucleic acid molecules and the splint nucleic acid molecules or renatured double-stranded nucleic acid molecules during the cyclizaiton reaction, thus significantly increasing the intramolecular self-ligation efficiency and self-cyclization efficiency of the single-stranded nucleic acid molecules compared to the prior art.

In a fourth aspect, the present disclosure in embodiments provides a sequencing library. In an embodiment, the sequencing library has a base separation rate of 0.5% or below. During the sequencing of the sequencing library according to the embodiment, the positive strand and negative strand are balanced, resulting in a low base separation rate for A and T (or a low base separation rate for G and C) such as 0.5% or below, thereby assuring a high accuracy of DNA quantification and SNP determination.

In a fifth aspect, the present disclosure in embodiments provides a sequencing library. In an embodiment, the sequencing library is obtained by the method as described in the third aspect. According to the sequencing library in the embodiment, the cyclized single-stranded nucleic acid molecules in the sequencing library display a high cyclizaiton rate.

In a sixth aspect, the present disclosure in embodiments provides a method for DNA sequence analysis in an embodiment, the method for DNA sequence analysis comprises sequencing the sequencing library as described in the fourth aspect or the fifth aspect so as to obtain sequencing results containing a plurality of sequencing reads; and aligning the sequencing results with a reference sequence so as to obtain DNA sequence information. According to the method in the embodiment, the DNA sequence information obtained has a high accuracy rate.

In a seventh aspect, the present disclosure in embodiments provides a kit. In an embodiment, the kit comprises the splint nucleic acid molecule as described in the first aspect. When the kit according to this embodiment is applied, the first complementary region and the second complementary region can be formed via annealing at different temperatures because of the length difference between the first complementary region and the second complementary region, thereby effectively avoiding the intermolecular ligation of the single-stranded nucleic acid molecules to be cyclized and effectively improving the self-cyclization efficiency of the single-stranded nucleic acid molecules to be cyclized.

In an eighth aspect, the present disclosure in embodiments provides a device for cyclizing a single-stranded nucleic acid molecule. In an embodiment, the device for cyclizing a single-stranded nucleic acid molecule is configured to allow a reaction mixture containing a splint nucleic acid molecule, a single-stranded nucleic acid molecule and a ligase to be under a condition suitable for ligation such that the single-stranded nucleic acid molecule is cyclized, so as to obtain a cyclized single-stranded nucleic acid molecule. According to the embodiment, the device is suitable to perform the method for cyclizing a single-stranded nucleic acid molecule as described in the second aspect, thus the formation of linear complexes of the single-stranded nucleic acid molecules and the splint nucleic acid molecules or renatured double-stranded nucleic acid molecules can be effectively avoided, thus significantly increasing the intramolecular self-ligation efficiency and self-cyclization efficiency of the single-stranded nucleic acid molecules.

In a ninth aspect, the present disclosure in embodiments provides a system for constructing a sequencing library. In an embodiment, the system for constructing a sequencing library comprises:

a device for cyclizing a single-stranded nucleic acid molecule, configured to subject a single-stranded nucleic acid molecule carrying an insert fragment to performing the method as described in the second aspect, thereby obtaining a product containing a cyclized single-stranded nucleic acid molecule carrying an insert fragment; and a digesting device, connected to the device for cyclizing a single-stranded nucleic acid molecule and configured to digest the product containing a cyclized single-stranded nucleic acid molecule carrying an insert fragment, so as to obtain a cyclized sequencing library;

wherein the single-stranded nucleic acid molecule carrying an insert fragment comprises an insert fragment, a first adaptor connected to a 5' terminal of the insert fragment, and a second adaptor connected to a 3' terminal of the insert fragment. According to the embodiment, the device is suitable to perform the method for constructing a sequencing library as described in the third aspect, which is capable of effectively avoiding the formation of linear complexes of the single-stranded nucleic acid molecules and the splint nucleic acid molecules or renatured double-stranded nucleic acid molecules during the cyclizaiton reaction, thus significantly increasing the intramolecular self-ligation efficiency and self-cyclization efficiency of the single-stranded nucleic acid molecules compared to the prior art.

In a tenth aspect, the present disclosure in embodiments provides a system for DNA sequence analysis. In an embodiment, the system for DNA sequence analysis comprises a sequencing device, configured to sequence the sequencing library as described in the forth aspect or the fifth aspect so as to obtain sequencing results containing a plurality of sequencing reads; and an aligning device, connected to the sequencing device and configured to align the sequencing results with a reference sequence so as to obtain DNA sequence information. According to the embodiment, the device is suitable to perform the method for DNA sequence analysis as described in the sixth aspect. The DNA sequence information obtained has a high accuracy rate.

The additional aspects and advantages of the present disclosure will be partly described the following description, and part of them will become apparent from the following description or be understood through the practice of the present disclosure.

BRIEF DESCRIPTION OF THE DRAWINGS

The above and/or additional aspects and advantages of the present disclosure will become apparent and easily understood from the description of the embodiments with reference to the drawings, in which.

DETAILED DESCRIPTION

The embodiments of the present disclosure are described in detail in the below and examples of the embodiments are shown in drawings. The exemplary embodiments described below with reference to the drawings are intended to explain the present disclosure and should not be construed as limiting the present disclosure.

Term Explanation

Figure 1:
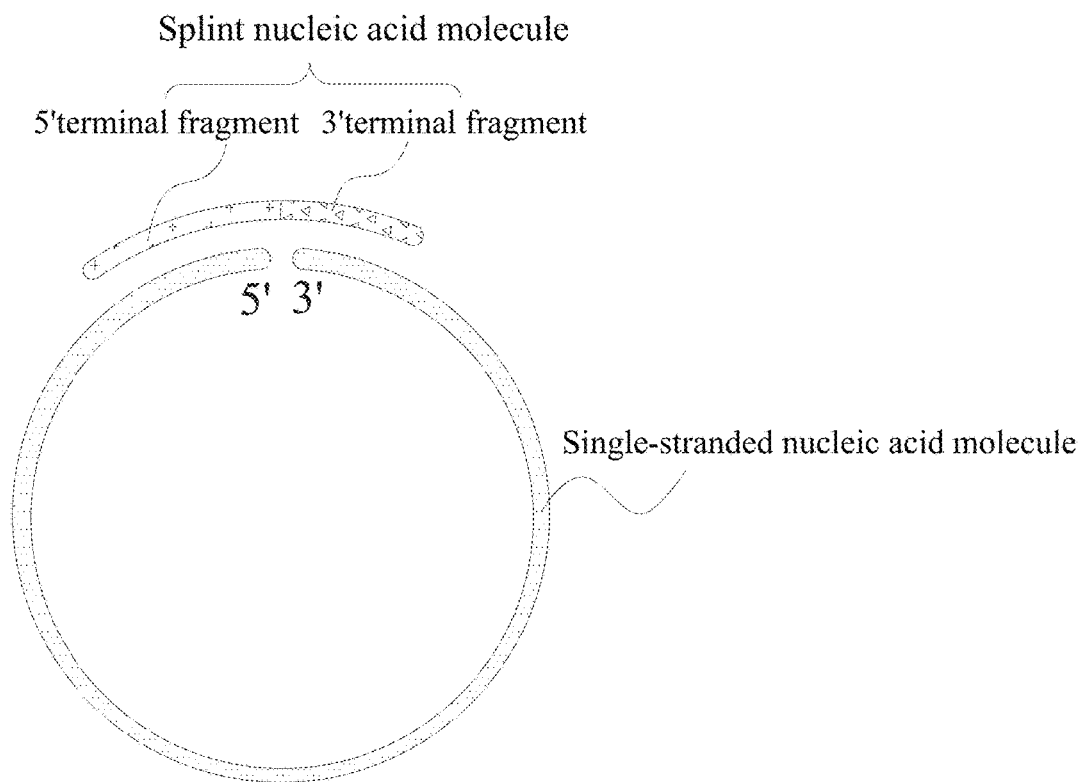
FIG. 1 is a schematic structural diagram of a splint nucleic acid molecule according to an embodiment of the present disclosure.

Unless otherwise specified, referring to FIG. 1, the "splint nucleic acid molecule" used herein refers to a nucleic acid molecule adapted to allow two terminals of a single-stranded nucleic acid molecule to be cyclized closed via two terminal fragments of the nucleic acid molecule, thereby improving the cyclization efficiency.

Unless otherwise specified, the "single-stranded nucleic acid molecule to be cyclized" or "single-stranded nucleic acid molecule" in short used herein refers to a nucleic acid molecule containing a single-stranded region, particularly two terminals of the nucleic acid molecule are single-stranded regions, preferably the entire sequence of the nucleic acid molecule is a single-stranded region.

Unless otherwise specified, the "5' terminal fragment" used herein refers to a region carrying 5'-phosphate group on the splint nucleic acid molecule, which cannot be understood as a free region.

Unless otherwise specified, the "3' terminal fragment" used herein refers to a region carrying 3'-hydroxyl on the splint nucleic acid molecule, which cannot be understood as a free region.

Unless otherwise specified, the "complementary region" used herein refers to a region containing a double-stranded structure formed via complementation of bases.

Unless otherwise specified, the "complementary region" used herein may contain a certain number of mismatched bases.

Unless otherwise specified, the number of mismatched bases as used herein is determined by a complementary region which contains the most number of unmatched bases (not forming a double-stranded structure) among the first and second complementary regions. For example, in a first complementary region formed between a 5' terminal fragment of the splint nucleic acid molecule and a 5' terminal of the single-stranded nucleic acid molecule, if the 5' terminal fragment and the 5' terminal of the single-stranded nucleic acid molecule respectively contain three unmatched bases and one unmatched base (not forming a double-stranded structure), it is considered that the first complementary region contains 3 mismatched bases.

Unless otherwise specified, the "thermostable ligase" used herein refers to a ligase which has an activity at a high temperature such as 95° C. and has the activity being 50%, 60%, 70%, 80%, 90%, 95%, 99% or 100% of the highest activity at a low temperature such as 37° C.

Unless otherwise specified, the "base separation" used herein refers to the fact that the content of A base occurring in various positions of sequenced reads is different with the content of T base in the same positions (or the content of C base is different with the content of G base) under biased sequencing, that is the so-called base separation. Theoretically, the probability of A base occurring in any position of sequenced reads is equal to the probability of T base in the same position (or the probability of C base is equal to the probability of G base) under enough randomness because of the complementation of double-stranded structure and the characters of bases on genome. The base separation rate is calculated as follows. Suppose the length of the sequenced read is L, starting from the base at the 11th position of the Read and ending at a position n (n is within the range of 11 to L), the total number of bases is divided by the absolute value of the number of A base minus the number of T base and expressed as percentage, Pn(|AT|), and the values are averaged, thus obtaining the base separation rate.

Unless otherwise specified, terms "first", "second", "third" and the like used herein are for the convenience of description and for distinguishing purposes, which do not explicitly or imply represent differences in order or importance between them for any purpose. Further, these terms do not mean that the contents defined by them consist of only one component.

Figure 2:
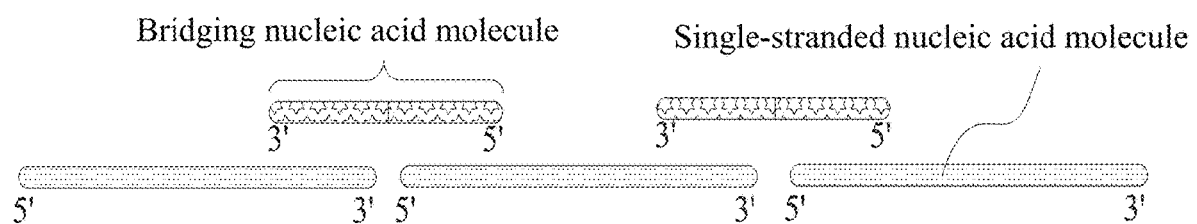
FIG. 2 is a schematic diagram of intermolecular ligation of single-stranded nucleic acid molecules mediated by a bridging nucleic acid molecule with a symmetric structure according to an embodiment of the present disclosure.

Splint Nucleic Acid Molecule for Cyclizing a Single-Stranded Nucleic Acid Molecule In a first aspect of the present disclosure, provided in embodiments is a splint nucleic acid molecule for cyclizing a single-stranded nucleic acid molecule. According to an embodiment, the splint nucleic acid molecule for cyclizing a single-stranded nucleic acid molecule consists of a 5' terminal fragment and a 3' terminal fragment, in which the 5' terminal fragment is adapted to form a first complementary region between the 5' terminal fragment and a 5' terminal of the single-stranded nucleic acid molecule, the 3' terminal fragment is adapted to form a second complementary region between the 3' terminal fragment and a 3' terminal of the single-stranded nucleic acid molecule, and a length of the first complementary region is different from a length of the second complementary region. The splint nucleic acid molecule according to the embodiment is an oligonucleotide sequence (i.e., splint oligo), which is suitable for construction of a cyclized sequencing library. According to the embodiment, the first complementary region and the second complementary region can be formed via annealing at different temperatures because of the length difference between the first complementary region and the second complementary region, thereby effectively avoiding the intermolecular ligation of the single-stranded nucleic acid molecules to be cyclized and effectively improving the self-cyclization efficiency of the single-stranded nucleic acid molecules to be cyclized. For clarity, referring to FIG. 1, the first and second complementary regions with different lengths form an asymmetric complementary structure. During the annealing of the splint nucleic acid molecule and the single-stranded nucleic acid molecule, the longer complementary region of the first and second complementary regions is firstly formed via annealing followed by formation of the shorter complementary region, thus facilitating the intramolecular self-ligation of the single-stranded nucleic acid molecules and significantly improving the self-cyclization efficiency of the single-stranded nucleic acid molecules. Referring to FIG. 2, a bridging nucleic acid molecule in the prior art and the single-stranded nucleic acid molecule form a first complementary region and a second complementary region with equal lengths. The first and second complementary regions with equal lengths form a symmetric complementary structure, which increases the intermolecular ligation, thereby generating increased mismatched linear complex structures rather than the required cyclized structures.

According to embodiments, the length of the first complementary region is equal to a length of the 5' terminal fragment, and the length of the second complementary region is equal to a length of the 3' terminal fragment. Thus, the 5' terminal and the 3' terminal of the single-stranded nucleic acid molecule are extremely close, which facilitates the ligation between the 5' terminal and the 3' terminal of the single-stranded nucleic acid molecule.

According to an embodiment, the length of the first complementary region is longer than the length of the second complementary region.

According to an embodiment, the length of the first complementary region is at least 1.5 times longer than the length of the second complementary region.

According to an embodiment, the length of the first complementary region is at least twice longer than the length of the second complementary region.

According to an embodiment, the length of the first complementary region is at least 10 by longer than the length of the second complementary region.

According to an embodiment, the length of the first complementary region is at least 13 bp longer than the length of the second complementary region.

According to an embodiment, melting temperature (Tm) values of the first complementary region and the second complementary region differ by 10° C. The present inventors have found that the Tm difference of 10° C. between the first complementary region and the second complementary region facilitates the formation of a two-stage gradient annealing, which improves the self-cyclization efficiency of the single-stranded nucleic acid molecules.

According to an embodiment, the 5' terminal fragment is of a length of 25 bp and the 3' terminal fragment is of a length of 11 bp. Thus, the 5' terminal fragment and the 5' terminal of the single-stranded nucleic acid molecule can be annealed at a higher temperature firstly, followed by annealing between the 3' terminal fragment and the 3' terminal of the single-stranded nucleic acid molecule at a lower temperature. Such a two-stage gradient annealing facilitates the intramolecular self-ligation of the single-stranded nucleic acid molecules, thereby significantly improving the self-cyclization efficiency of the single-stranded nucleic acid molecules.

Figures 3, 4:
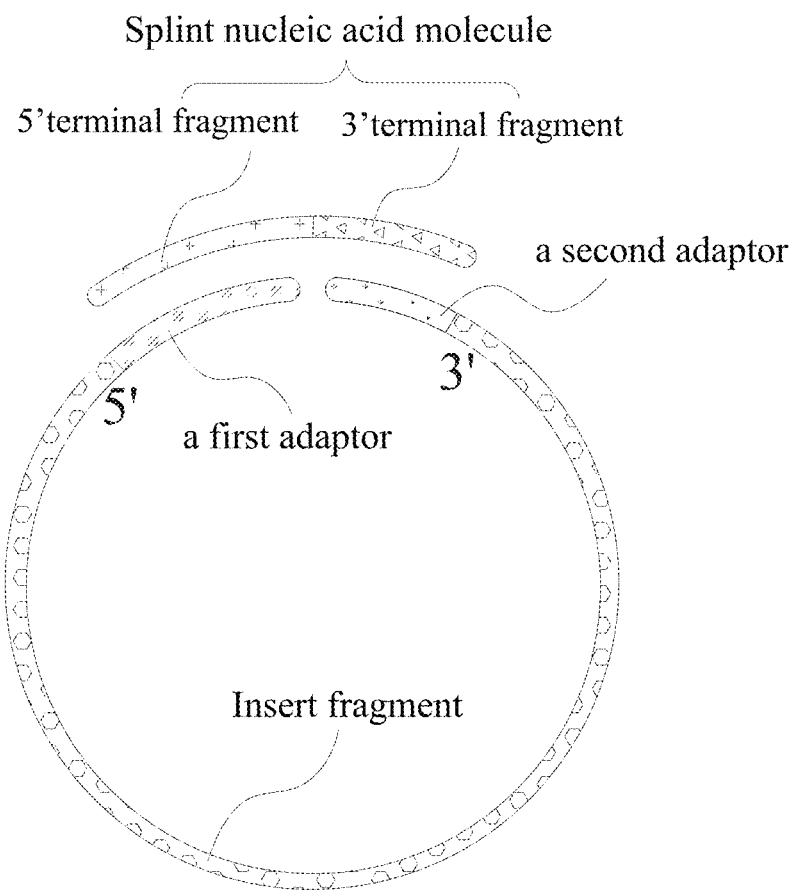
FIG. 3 is a schematic structural diagram of a complex of a single-stranded nucleic acid molecule and a splint nucleic acid molecule according to an embodiment of the present disclosure.
FIG. 4 is a schematic diagram of a system for constructing a sequencing library according to an embodiment of the present disclosure.

According to an embodiment, referring to FIG. 3, the single-stranded nucleic acid molecule comprises an insert fragment, a first adaptor connected to a 5' terminal of the insert fragment, and a second adaptor connected to a 3' terminal of the insert fragment. The 5' terminal fragment of the splint nucleic acid molecule is adapted to form the first complementary region between the 5' terminal fragment and at least a part of the first adaptor and the 3' terminal fragment of the splint nucleic acid molecule is adapted to form the second complementary region between the 3' terminal fragment and at least a part of the second adaptor. Thus, the single-stranded nucleic acid molecule after cyclization reaction can be useful in library construction and sequencing analysis.

It should be noted that the provision forms of the insert fragment according to the present disclosure is not particularly limited. The insert fragment can be obtained by interrupting and denaturing genomic DNA. The insert fragment can be directly provided in the form of single-stranded DNA or RNA. The insert fragment can also be a recombinant nucleic acid molecule obtained by inserting a target nucleic acid molecule into a nucleic acid vector. According to a specific embodiment, the insert fragment is derived from at least a part of a genomic fragment. Specifically, the genomic fragment is obtained by interrupting and denaturing genomic DNA. Thus, the single-stranded nucleic acid molecules derived from the genomic DNA can be cyclized by the splint nucleic acid molecule according to the embodiments, thereby obtaining a genomic sequencing library.

According to an embodiment, the insert fragment is of a length of 100 to 600 bp. The splint nucleic acid molecule according to the embodiments is not only suitable for the construction of a DNA library with an insert fragment of 100 to 300 bp, but also suitable for the construction of a DNA library with a larger insert fragment such as 300 to 600 bp. Thus, when the splint nucleic acid molecule according to the embodiments of the present disclosure is used for the construction of a DNA library with an insert fragment of 100 to 600 bp, the single-stranded nucleic acid molecules can be cyclized in high cyclization efficiency, with the DNA library in a low base separation rate.

According to a specific embodiment, the single-stranded nucleic acid molecule comprises a first adaptor and a second adaptor. The first adaptor is connected to a 5' terminal of the insert fragment and the second adaptor is connected to a 3' terminal of the insert fragment. The single-stranded nucleic acid molecule is of a length of 136 to 636 bp.

According to an embodiment, the 5' terminal fragment is of the nucleotide sequence of SEQ ID NO: 1.

(SEQ ID NO: 1)
AAGTCGGATCGTAGCCATGTCGTT.

The 5' terminal fragment in the embodiment as described above is capable of complementarily pairing with the 5' terminal of the single-stranded nucleic acid molecule at a temperature of 35 to 65° C.

According to an embodiment, the 3' terminal fragment is of the nucleotide sequence of SEQ ID NO: 2.

(SEQ ID NO: 2)
TGTGAGCCAAG.

The 3' terminal fragment in the embodiment as described above is capable of complementarily pairing with the 3' terminal of the single-stranded nucleic acid molecule at a temperature of 32 to 42° C.

According to an embodiment, the splint nucleic acid molecule is of the nucleotide sequence of SEQ ID NO: 3.

(SEQ ID NO: 3)
AAGTCGGATCGTAGCCATGTCGTTCTGTGAGCCAAG.

According to the splint nucleic acid molecule in the embodiments as described above, its 5' terminal fragment can be paired with the single-stranded nucleic acid molecule via annealing at a first temperature and its 3' terminal fragment can be paired with the single-stranded nucleic acid molecule via annealing at a second different temperature, thereby avoiding the formation of linear complexes of the single-stranded nucleic acid molecules and the splint nucleic acid molecules or renatured double-stranded nucleic acid molecules as much as possible, thus significantly increasing the self-cyclization efficiency of the single-stranded nucleic acid molecules.

According to an embodiment, the splint nucleic acid molecule is DNA.

According to an embodiment, the first complementary region and the second complementary region each independently comprise 5 mismatched bases or below, preferably 4 mismatched bases or below, preferably 3 mismatched bases or below; preferably 2 mismatched bases or below, preferably 1 mismatched base or below, more preferably no mismatched base. The present inventors have found that the splint nucleic acid molecule and the single-stranded nucleic acid molecule can be annealed successfully and effectively and the single-stranded nucleic acid molecule can be cyclized in a high self-cyclization efficiency when the number of the mismatched bases of the the first and second complementary regions is five or below. Further, fewer mismatched bases of the first and second complementary regions, higher efficiency of annealing between the splint nucleic acid molecule and the single-stranded nucleic acid molecule and higher self-cyclization efficiency for the single-stranded nucleic acid molecule.

Method for Cyclizing a Single-Stranded Nucleic Acid Molecule

In a second aspect of the present disclosure, provided in embodiments is a method for cyclizing a single-stranded nucleic acid molecule. According to an embodiment, the method comprises allowing a reaction mixture containing a splint nucleic acid molecule, a single-stranded nucleic acid molecule and a ligase to be under a condition suitable for ligation, so as to obtain a cyclized single-stranded nucleic acid molecule. According to the method in this embodiment, it is possible to effectively avoid the formation of linear complexes of the single-stranded nucleic acid molecules and the splint nucleic acid molecules or renatured double-stranded nucleic acid molecules, thus significantly increasing the intramolecular self-ligation efficiency and self-cyclization efficiency of the single-stranded nucleic acid molecules compared to the prior art.

According to an embodiment, the ligase is a thermostable ligase. It should be noted that the "thermostable ligase" used herein refers to a ligase which has an activity at a high temperature such as 95° C. and has the activity being 50%, 60%, 70%, 80%, 90%, 95% or 99% of the highest activity at a low temperature such as 37° C.

According to a specific embodiment, the thermostable ligase is capable of resisting a temperature of at least 50° C., preferably at least 70° C., preferably at least 80° C., more preferably at least 90° C. Thus, the complementarily pairing between the single-stranded nucleic acid molecule and the splint nucleic acid molecule can be mediated by the thermostable ligase at a high temperature such as 50° C. The thermostable ligase is capable of reducing the generation of DNA secondary structure and facilitates a higher specificity at a high temperature, such as Taq DNA ligase capable of annealing at 50° C. In contrast, original 14 ligase allows an oligonucleotide strand to be annealed with a template strand at 37° C., which more easily generates mismatched secondary structure and causes mismatched ligation.

According to an embodiment, the thermostable ligase is Tag DNA ligase. When a conventional ligase such as T4 DNA ligase is used for DNA ligation, two DNA molecules can be ligated as long as 5'-phosphate terminal and 3'-hydroxyl terminal are presented. In contrast, Taq DNA ligase is a high-fidelity ligase, with a high fidelity. Specifically, the Taq DNA ligase relies on an oligonucleotide chain (i.e., oligo) for ligation, and the presence of any base mismatched to corresponding complementary strand in the oligo chain would result in failure of ligation. Thus, use of Taq DNA ligase in the embodiment of the present disclosure significantly reduces the mismatch rate.

According to an embodiment, the method for cyclizing a single-stranded nucleic acid molecule comprises steps:

(1) allowing the reaction mixture to be at a first temperature for a first predetermined time, in which the first temperature is suitable to form a first complementary region between a 5' terminal fragment of the splint nucleic acid molecule and a 5' terminal of the single-stranded nucleic acid molecule, (2) allowing the reaction mixture obtained in step (1) to be at a second temperature for a second predetermined time, in which the second temperature is suitable to form a second complementary region between a 3' terminal fragment of the splint nucleic acid molecule and a 3' terminal of the single-stranded nucleic acid molecule, (3) allowing the reaction mixture obtained in step (2) to be at a third temperature for a third predetermined time, in which the third temperature is suitable to unwind at least one of the first complementary region and the second complementary region, and (4) subjecting the reaction mixture obtained in step (3) to performing steps (1) and (2) in sequence. According to the method as described in the embodiment, the uncyclized nucleic acid molecules, such as linear complexes of the single-stranded nucleic acid molecules and the splint nucleic acid molecules or renatured double-stranded nucleic acid molecules can be unwinded followed by re-annealing, thus significantly improving the ligation efficiency and reducing ligation bias.

According to an embodiment, the method further comprises (5) subjecting the reaction mixture obtained in step (4) to performing steps (3), (1) and (2) in sequence for at least one cycle. The present inventors have found that the ligation reaction is a dynamic process, during which the reactants (i.e., the splint nucleic acid molecule and the single-stranded nucleic acid molecule) in the reaction mixture solution collide with each other to generate a ligated product under the action of driving force and ligase. The reactants having different GC contents require different energy and driving force for ligation, and the ligated products would not be increased when arrived at an equilibrium state. However, in the case that several rounds of ligation reaction as described above are performed, the unligated nucleic acid molecules at an equilibrium state in the first round would be involved in a ligation reaction in a second round, which is same for the subsequent rounds, thus most nucleic acid molecules would reach a relatively equilibrium state finally. Therefore, the method as described above can achieve a maximum cyclization efficiency and significantly reduce the base separation.

According to an embodiment, the method for cyclizing a single-stranded nucleic acid molecule further comprises subjecting the reaction mixture obtained in step (4) to performing steps (3), (1) and (2) in sequence for 2 to 18 cycles in step (5). The present inventors have found that all the nucleic acid molecules would reach a relatively equilibrium state after 4 to 20 cycles of the ligation reaction as described above, thus achieving a high cyclization efficiency and significantly reduced base separation.

According to an embodiment, the single-stranded nucleic acid molecule is obtained by denaturing a sample containing double-stranded nucleic acid molecules.

According to a specific embodiment, the denaturing is performed at a temperature of 95° C. for 3 to 5 minutes, thus the secondary structures of double-stranded nucleic acid molecules are opened and the single-stranded nucleic acid molecules are generated.

Further, the present inventors have also found that the greater the difference of annealing temperature between the first complementary region and the second complementary region, the less formation of intermolecular ligation of the single-stranded nucleic acid molecules. Meanwhile, it should be noted that the different between the annealing temperature of the second complementary region and the optimal temperature of the ligase is necessary to be in a reasonable range. Thus, the temperatures should be chosen carefully.

According to an embodiment, the first temperature is higher than the second temperature.

According to a specific embodiment, an activity of the ligase at the second temperature is 50% or above of the highest activity, preferably 80% or above, preferably 90% or above, preferably 91% or above, preferably 92% or above, preferably 93% or above, preferably 94% or above, preferably 95% or above, preferably 96% or above, preferably 97% or above, preferably 98% or above, preferably 99% or above, more preferably 100% of the highest activity.

According to a specific embodiment, a difference between the second temperature and an optimal temperature of the ligase is 10° C. or below, preferably 8° C. or below, preferably 5° C. or below, preferably 4° C. or below, preferably 3° C. or below, more preferably 2° C. or below. Among them, the "optimal temperature" refers to a temperature when the ligase exhibits highest activity. For example, the optimal temperature of the Taq DNA ligase used in the specific embodiment is 45° C.

According to a specific embodiment, the second temperature is lower than the optimal temperature of the ligase, and the second temperature is 2 to 8° C. lower than the optimal temperature of the ligase.

The present inventors have also found that the first temperature and the second temperature within the temperature difference range as described above are suitable to form the first complementary region and the second complementary in two stages, thus preventing the intermolecular ligation of the single-stranded nucleic acid molecules. Further, the difference between the second temperature and the optimal temperature of the ligase is within a reasonable range suitable for the annealing of the second complementary region.

According to an embodiment, the first temperature is 35 to 65° C. and the first predetermined time is 2 minutes, preferably the first temperature is 50° C. Thus, the 5' terminal fragment of the splint nucleic acid molecule can be completely complementary to the 5' terminal of the single-stranded nucleic acid molecule and the first complementary region between the 5' terminal fragment and the 5' terminal of the single-stranded nucleic acid molecule is formed.

According to an embodiment, the second temperature is 32 to 42° C. and the second predetermined time is 30 minutes, preferably the second temperature is 37° C. Thus, the 3' terminal fragment of the splint nucleic acid molecule can be completely complementary to the 3' terminal of the single-stranded nucleic acid molecule and the second complementary region between the 3' terminal fragment and the 3' terminal of the single-stranded nucleic acid molecule is formed.

According to an embodiment, the third temperature is 94 to 98° C. and the third predetermined time is 30 seconds, preferably the third temperature is 95° C. Thus, the double-stranded nucleic acid molecules generated in the reaction mixture solution can be completely unwound, followed by re-annealing in a new round of ligation reaction, which is same for subsequent rounds, thus achieving a maximum cyclization efficiency and significantly reducing the base separation.

Method for Constructing a Sequencing Library

In a third aspect of the present disclosure, provided in embodiments is a method for constructing a sequencing library. According to an embodiment, the method for constructing a sequencing library comprises subjecting a single-stranded nucleic acid molecule carrying an insert fragment to performing the method as described in the second aspect, thereby obtaining a product containing a cyclized single-stranded nucleic acid molecule carrying an insert fragment; and digesting the product containing a cyclized single-stranded nucleic acid molecule carrying an insert fragment, so as to obtain a cyclized sequencing library. Among them, the single-stranded nucleic acid molecule carrying an insert fragment comprises an insert fragment, a first adaptor connected to a 5' terminal of the insert fragment, and a second adaptor connected to a 3' terminal of the insert fragment. According to the method in the embodiment, the formation of linear complexes of the single-stranded nucleic acid molecules and the splint nucleic acid molecules or renatured double-stranded nucleic acid molecules can be effectively avoided during the cyclizaiton reaction, thereby significantly increasing the self-ligation efficiency and self-cyclization efficiency of the single-stranded nucleic acid molecule compared to the prior art.

According to an embodiment, the digesting is performed under the action of DNA exonuclease. Thus, the uncyclized single-stranded nucleic acid molecules and the renatured double-stranded nucleic acid molecules formed during the cyclization reaction can be digested, thereby increasing the cyclization degree of the sequencing library.

According to an embodiment, the DNA exonuclease comprises exonuclease I and exonuclease Ill. The exonuclease I is capable of hydrolyzing the uncyclized single-stranded nucleic acid molecules and the exonuclease III is capable of hydrolyzing single nucleotides at the 3' terminal of the double-stranded nucleic acid molecules, therefore only cyclized single-stranded nucleic acid molecules are retained after the digesting.

According to an embodiment, the digesting is performed at 37° C. for 30 minutes. Thus, the uncyclized single-stranded nucleic acid molecules and the renatured double-stranded nucleic acid molecules can be completely digested, avoiding excessive digestion reaction and generation of non-target products.

According to an embodiment, the method for constructing a sequencing library further comprises subjecting a digested product to fourth purification after the digesting, thus eliminating the interference of enzymes or ions for the cyclization reaction and the digestion reaction on subsequent library construction or sequencing, thereby further improving the purity of the cyclized sequencing library and the accuracy of the sequencing results.

According to an embodiment, the single-stranded nucleic acid molecule carrying an insert fragment is obtained by steps of subjecting a genomic sample to random interruption, first purification, end repair and adaptor addition, in which the adaptor comprises the first adaptor and the second adaptor; subjecting the genomic sample connected with adaptor to second purification and PCR amplification; and subjecting a PCR amplified product to third purification and denaturation, so as to obtain a denatured product, in which the denatured product is the single-stranded nucleic acid molecule carrying an insert fragment.

According to a specific embodiment, the denaturation is performed at a temperature of 95° C. for 3 to 5 minutes, thus the PCR amplified product can be completely unwound and a single-stranded genomic sample is obtained.

According to an embodiment, the method for constructing a sequencing library further comprises subjecting the cyclized sequencing library to DNA nanoball (DNB) amplification so as to obtain a DNB sequencing library. Specifically, the DNB amplification treatment includes the following steps. The cyclized DNA library (i.e., cyclized single-stranded nucleic acid molecules) is supplemented with water and DNA nanoball (DNB) preparation buffer, vortexed to mix, centrifuged briefly and reacted on the PCR machine according to the procedure of 95° C. for 1 min, 65° C. for 1 min, 40° C. for 1 min and holding at 4° C. After that, the PCR tube at 4° C. is taken out, DNB polymerase mixture I and DNB polymerase mixture H are added, vortexed to mix, centrifuged briefly and then reacted on the PCR machine according to the procedure of 30° C. for 20 mins and holding at 4° C. After completion of the reaction, the PCR tube at 4° C. is transferred into an ice box and DNB stop buffer is added, which is gently pipetted by the pipette and widemouth pipette tip to mix. Thus, the DNB sequencing library is obtained, which is stored at 4° C. for use.

Sequencing Library

In a fourth aspect of the present disclosure, provided in embodiments is a sequencing library. According to an embodiment, the sequencing library has a base separation rate of 0.5% or below. During the sequencing of the sequencing library according to the embodiment, the positive strand and negative strand are balanced, resulting in a low base separation rate for A and T (or a low base separation rate for G and C) such as 0.5% or below, thusassuing a high accuracy of DNA quantification and SNP determination.

In a fifth aspect of the present disclosure, provided in embodiments is a sequencing library. According to an embodiment, the sequencing library is obtained by the method as described in the third aspect. According to sequencing library in the embodiment, the cyclized single-stranded nucleic acid molecules in the sequencing library display a high cyclizaiton rate and a base separation rate of 0.5% or below.

Method for DNA Sequence Analysis

In a sixth aspect of the present disclosure, provided in embodiments is a method for DNA sequence analysis. According to an embodiment, the method for DNA sequence analysis comprises sequencing the sequencing library as described in the fourth aspect or the fifth aspect, so as to obtain sequencing results containing a plurality of sequencing reads; and aligning the sequencing results with a reference sequence so as to obtain DNA sequence information. According to the method in the embodiment, the DNA sequence information obtained has a high accuracy rate.

Kit

In a seventh aspect of the present disclosure, provided in embodiments is a kit. According to an embodiment, the kit comprises the splint nucleic acid molecule as described in the first aspect. When the kit according to this embodiment is applied, the first complementary region and the second complementary region can be formed via annealing at different temperatures because of the length difference between the first complementary region and the second complementary region, thereby effectively avoiding the intermolecular ligation of the single-stranded nucleic acid molecules to be cyclized and effectively improving the self-cyclization efficiency of the single-stranded nucleic acid molecules to be cyclized.

Device for Cyclizing a Single-Stranded Nucleic Acid Molecule

In an eighth aspect of the present disclosure, provided in embodiments is a device for cyclizing a single-stranded nucleic acid molecule. According to an embodiment, the device for cyclizing a single-stranded nucleic acid molecule is configured to allow a reaction mixture containing a splint nucleic acid molecule, a single-stranded nucleic acid molecule and a ligase to be under a condition suitable for ligation such that the single-stranded nucleic acid molecule is cyclized, so as to obtain a cyclized single-stranded nucleic acid molecule. According to the device in the embodiment, the formation of linear complexes of the single-stranded nucleic acid molecules and the splint nucleic acid molecules or renatured double-stranded nucleic acid molecules can be effectively avoided, thus significantly increasing the self-ligation efficiency and self-cyclization efficiency of the single-stranded nucleic acid molecules.

The device as described in the embodiment is suitable to perform the method for cyclizing a single-stranded nucleic acid molecule in the embodiment of the second aspect. The additional technical features, advantages and effects of this device are same as those described for the method for cyclizing a single-stranded nucleic acid molecule in the embodiments as described above.

System for Constructing a Sequencing Library

In a ninth aspect of the present disclosure, provided in embodiments is a system for constructing a sequencing library. According to an embodiment, referring to FIG. 4, the system for constructing a sequencing library comprises a device 100 for cyclizing a single-stranded nucleic acid molecule, configured to subject a single-stranded nucleic acid molecule carrying an insert fragment to performing the method for cyclizing a single-stranded nucleic acid molecule as described in the second aspect, thereby obtaining a product containing a cyclized single-stranded nucleic acid molecule carrying an insert fragment; and a digesting device 200, connected to the device 100 for cyclizing a single-stranded nucleic acid molecule and configured to digest the product containing a cyclized single-stranded nucleic acid molecule carrying an insert fragment, so as to obtain a cyclized sequencing library. Among them, the single-stranded nucleic acid molecule carrying an insert fragment comprises an insert fragment, a first adaptor connected to a 5' terminal of the insert fragment, and a second adaptor connected to a 3' terminal of the insert fragment.

Figure 5:
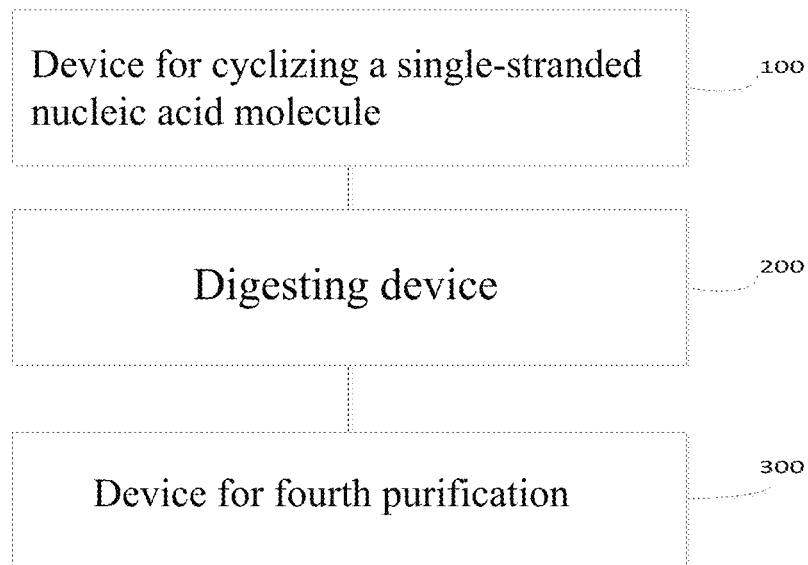
FIG. 5 is a schematic diagram of a system for constructing a sequencing library according to another embodiment of the present disclosure.

According to a further embodiment, referring to FIG. 5, the system further comprises a device 300 for fourth purification, connected to the digesting device 200 and configured to subject a digested product to fourth purification.

Figure 6:
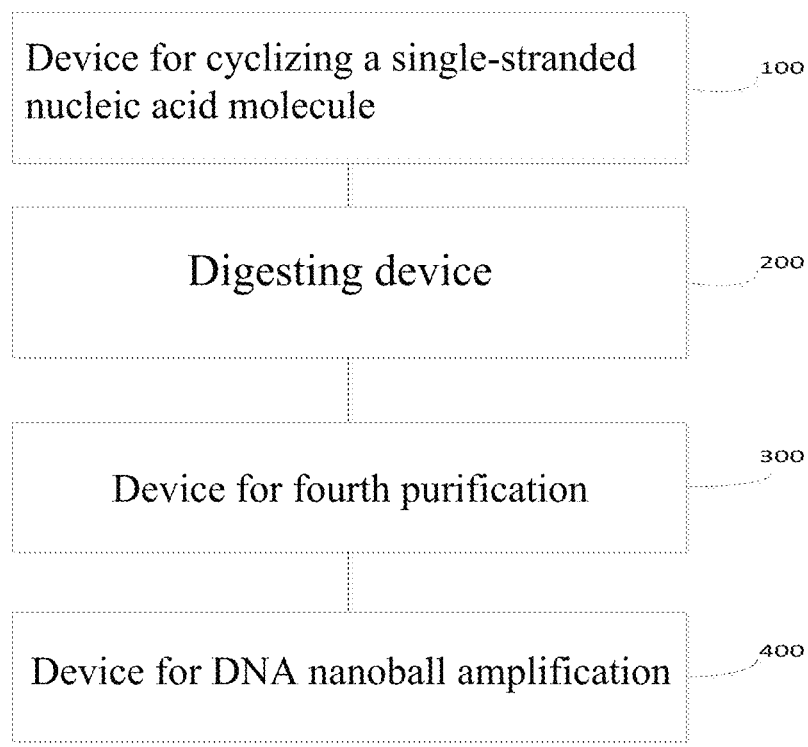
FIG. 6 is a schematic diagram of a system for constructing a sequencing library according to another embodiment of the present disclosure.

According to a further embodiment, referring to FIG. 6, the system further comprises a device 400 for DNA nanoball (DNB) amplification, configured to subject the cyclized sequencing library to DNB amplification so as to obtain a DNB sequencing library.

The system as described in the embodiment is suitable to perform the method for constructing a sequencing library in the embodiments of the third aspect. The additional technical features, advantages and effects of this system are same as those described for the method for constructing a sequencing library in the embodiments as described above.

System for DNA Sequence Analysis

Figure 7:
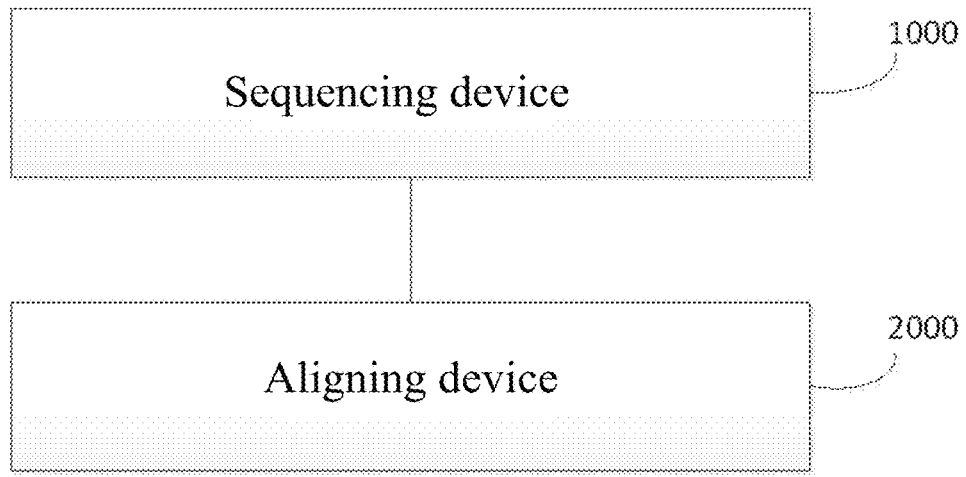
FIG. 7 is a schematic diagram of a system for DNA sequence analysis according to an embodiment of the present disclosure.

In a tenth aspect of the present disclosure, provided in embodiments is a system for DNA sequence analysis. According to an embodiment, referring to FIG. 7, the system for DNA sequence analysis comprises a sequencing device 1000, configured to sequence the sequencing library as described in the forth aspect or the fifth aspect so as to obtain sequencing results containing a plurality of sequencing reads; and an aligning device 2000, connected to the sequencing device 1000 and configured to align the sequencing results with a reference sequence so as to obtain DNA sequence information. According to the embodiment, the device is suitable to perform the method for DNA sequence analysis in the embodiments of the sixth aspect. The additional technical features, advantages and effects of this system are same as those described for the method for DNA sequence analysis in the embodiments as described above.

In summary, the inventors of the present disclosure provided the following solutions to improve the cyclization efficiency of single-stranded nucleic acid molecules during the library construction, which facilitate more single-stranded nucleic acid molecules to be self-ligated and cyclized. For this, one the one hand, the method of the present disclosure increases the ligation reaction rounds for improving cyclization of single-stranded nucleic acid molecules, in which the uncyclized linear complexes of the single-stranded nucleic acid molecules and the splint nucleic acid molecules or renatured double-stranded nucleic acid molecules generated after one round of ligation are unwinded via denaturation reaction, followed by re-annealing with the splint nucleic acid molecule having an asymmetric structure in a new round such that the unwinded single-stranded nucleic acid molecule is re-ligated and cyclized, which is same for subsequent rounds, thus achieving a maximum cyclization efficiency through several rounds of ligation. On the other hand, Taq DNA ligase, a thermostable ligase and having activity at a high temperature, is applied in the present disclosure, which can resist the high temperature for the several denaturation reactions performed in the present method, while T4 DNA ligase which cannot resist the high temperature for the several denaturation reactions is applied in the cyclizaiton reaction for the library construction in the prior art. In the present disclosure, Taq DNA ligase rather than T4 DNA ligase is applied for cyclizaiton of the single-stranded nucleic acid molecules, which not only reduces the mismatch rate, but also allows several rounds of ligation performed via denaturation at a high temperature and re-annealing so as to achieve a maximum cyclization efficiency.

Therefore, the technical solution proposed in embodiments of the present disclosure exhibits the following beneficial effects.

(1) Use of Taq DNA ligase for cyclizing a single-stranded nucleic acid molecule allows unwinding a double-stranded nucleic acid molecule at a high temperature and performing several rounds of ligation, such that each single-stranded nucleic acid molecule can be reacted fully and uniformly when mediated by the Tag DNA ligase, thereby increasing the ligation efficiency and significantly reducing the base separation during sequencing.

(2) The splint nucleic acid molecule splint oligo) and adaptors of the single-stranded nucleic acid molecule form an asymmetric complementary structure. For example, the first 25 bases of the splint oligo are completely complementary to one adaptor of the single-stranded nucleic acid molecule at one terminal, and the last 11 bases of the splint oligo are completely complementary to another adaptor of the single-stranded nucleic acid molecule at another terminal. Thus, an asymmetric complementary structure which is more stable is formed via annealing, which contributes to the intramolecular ligation of the single-stranded nucleic acid molecule.

(3) The method for cyclizing a single-stranded nucleic acid molecule provided in embodiments of the present disclosure is capable of reducing the base separation rate of DNA library during the next-generation sequencing, such as 0.5% or below of base separation rate, thereby improving the sequencing quality.

(4) The present disclosure is not only suitable for construction of a library of insert fragments in a length of 100 to 300 bp, but also suitable for construction of a library of large insert fragments such as in a length of 300 to 600 hp.

Reference will be made in detail to examples of the present disclosure. It would be appreciated by those skilled in the art that the following examples are explanatory and cannot be construed as limiting the scope of the present disclosure. If the specific technology or conditions are not specified in the examples, a step will be performed in accordance with the techniques or conditions described in the literature in the art (for example, referring to J. Sambrook, et al. (translated by Huang PT), *Molecular Cloning: A Laboratory Manual*, 3rd Ed., Science Press) or in accordance with the product instructions. If the manufacturers of reagents or instruments are not specified, the reagents or instruments may be commercially available, for example, from Illumina Company.

Figure 8:
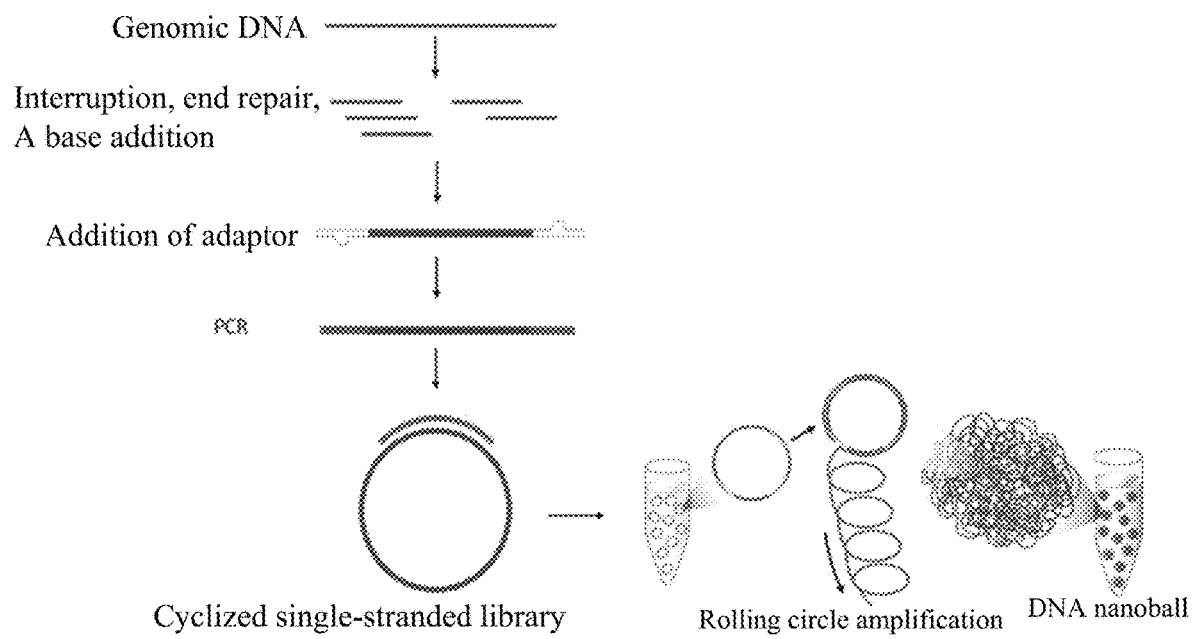
FIG. 8 is a schematic flow chart of the overall construction of a DNB sequencing library according to an embodiment of the present disclosure.

In the following examples, referring to FIG. 8, the overall flow chart of constructing a DNB sequencing library is illustrated.

EXAMPLE

In this example, human derived standard DNA (NA12878) was subjected to DNA sequencing library construction followed by sequencing by the present inventors, in which the method for cyclizing a single-stranded nucleic acid molecule provided in the present disclosure was adopted. The specific steps are as follows.

1) Sample Interruption

1 μg of genomic DNA in 80 μl of interruption reaction volume was interrupted into DNA fragments of 100 to 600 bp (≈200 bp of main band) by the Covaris E210.

The interruption parameters are below:

| | |
|---|---|
| Duty/cycle (0%) | 10 |
| Intensity | 5 |
| Cycle/burst | 200 |

| Time (s) | 60 |
| Cycle (s) | 5 |

2) Purification of Interrupted DNA

AMPure XP magnetic beads were placed at room temperature for 30 minutes before use, followed by thoroughly shaking and mixing. 80 μl of the pretreated. AMPure XP magnetic beads were transferred into a first PCR tube containing 80 μl of interrupted DNA obtained in step 1), which was gently pipetted by a pipette for 10 times to thoroughly mix, followed by incubation at room temperature for 5 minutes. Subsequently, the first PCR tube was centrifuged instantaneously, stood on a magnetic stand and stilled for 2 minutes to allow the liquid to be clear. About 160 μl of supernatant in the first PCR tube was transferred into a second new PCR tube by the pipette while the first PCR tube was kept on the magnetic stand. The second PCR tube was added with 40 μl AMPure XP magnetic beads, gently pipetted by the pipette for 10 times to thoroughly mix, and incubated at room temperature for 5 minutes. Subsequently, the second PCR tube was centrifuged instantaneously, stood on the magnetic stand and stilled for 2 minutes to allow the liquid to be clear, after which the supernatant in this tube was discarded by the pipette while the tube was kept on the magnetic stand. 500 μl of freshly prepared 80% ethanol was added into each of the first and second PCR tubes, incubated at room temperature for 1 minute and then the supernatant was discarded, while the first and second PCR tubes were kept on the magnetic stand. The step was repeated, after which the supernatant was discarded as much as possible. The lips of tubes were opened respectively for drying at room temperature for 3 minutes. Subsequently, the tubes were removed from the magnetic stand, 42 μl of TE buffer was added into each tube for DNA elution, pipetted by the pippte to mix and then incubated at room temperature for 5 minutes for DNA dissolution. The first and second PCR tubes were centrifuged instantaneously, stood on the magnetic stand and stilled for 2 minutes to allow the liquid to be clear, after which about 40 μl of supernatant in each tube was transferred into a new PCR tube while the first and second PCR tubes were kept on the magnetic stand.

3) End Repair 50 ng of purified DNA fragments obtained in were transferred into a new PCR tube based on the concentration. Nuclease-free (NF) water was added to a total volume of 40 μl, and then 10 μl of DNA library end repair reaction solution for BGI platforms (BGISEQ500 and MG12000) was added, which was reacted at 37° C. for 30 minutes, After that, the reactants were reacted at 65° C. for 15 minutes to deactivate the enzyme, followed by cooling to 4° C. at a rate of 0.1° C./second.

4) Addition of Adaptor

5 μl of adaptor mixture (the adaptor containing at least 8 types of tags) and 25 μl of ligase reaction solution were added to the reactant solution in 3), followed by incubated at 23° C. for 1 hour and making up to a volume of 100 μl with water, Ampure XP beads in a usage amount of 0.5× (50 μl) were added for purification.

5) Purification of DNA Connected with Adaptor

Ampure XP beads in a usage amount of 0.5× (50 μl) were used for purification.

6) PCR Reaction

PCR reaction solution was added to the purified DNA connected with adaptor obtained in 5), with a total volume of 100 μl. The PCR reaction was performed on the PCR machine according to the procedure:

| 95° C. | | 3 mins | |
| 98° C. | 20 s | | 6 cycles |
| 60° C. | 15 s | | |
| 72° C. | 30 s | | |
| 72° C. | | 5 mins | |
| 4° C. | | holding | |

7) Purification of PCR Product

After the completion of PCR reaction in 6), Ampure XP beads in a usage amount of 1× (100 μl) were used for purification of the PCR product.

8) Denaturation of PCR Product

Purified PCR product obtained in 7) was subjected to Qubit concentration detection. Subsequently. 330 ng of the PCR product was supplemented with TE buffer to 60 μl, and then 10 μl of splint nucleic acid molecule (10 μM, with a nucleotide sequence shown in SEQ ID NO: 3) was added and mixed. The solution was placed on the PCR machine and incubated at 95° C. for 3 to 5 minutes to allow the double-stranded DNA to be denatured into single-stranded DNA, immediately transferred into ice and stilled for 2 minutes.

(SEQ ID NO: 3)
AAGTCGGATCGTAGCCATGTCGTTCTGTGAGCCAAG.

9) Cyclization

A cyclization reaction mixture containing 12 μl× Taq DNA ligation buffer, 2 μl Taq DNA ligase (NEB, 40 U/μl) and 36 μl NF water was formulated, which was added into 70 μl of the denatured DNA solution obtained in 8) and performed the cyclization reaction on the PCR machine according to the procedure:

| 95° C. | 30 s | 4 cycles |
| 50° C. | 2 mins | |
| 37° C. | 30 mins | |
| 4° C. | holding | |

10) Digestion

A digestion reaction mixture containing 0.8 μl 10× digestion buffer, 3.9 μl exonuclease I, 1.3 μl exonuclease III and 2 μl NF water was formulated, which was added into 120 μl of cyclization reaction solution obtained in 9) and performed the digestion reaction on the PCR machine according to the procedure:

| 37° C. | 30 mins |
| 4° C. | holding |
| Addtion of 15 μl stop buffer to stop the digestion reaction | |

11) Purification of Digested Product

Ampure XP beads in a usage amount of 1.2× (170 μl) were used for purification of the digested product. The concentration of cyclized single-stranded nucleic acid molecules was detected by Qubit ssDNA Kit to be higher than 0.78 ng/μl. The product was stored at −20° C. for use.

12) DNB Preparation 6 ng of cyclized. DNA library (i.e., cyclized single-stranded nucleic acid molecules) obtained in 11) was supplemented with water to 20 μl, followed by addition of 20 μl of DNA nanoball (DNB) preparation buffer, vortexed to mix, centrifuged briefly and reacted on the PCR machine according to the procedure of 95° C. for 1 min, 65° C. for 1 min, 40° C. for 1 min and holding at 4° C. After that, the PCR tube at 4° C. was taken out, 40 μl of DNB polymerase mixture I and 4 μl of DNB polymerase mixture II were added, vortexed to mix, centrifuged briefly and then reacted on the PCR machine according to the procedure of 30° C. for 20 mins and holding at 4° C. After completion of the reaction, the PCR tube at 4° C. was transferred into an ice box and 20 μl of DNB stop buffer was added, which was gently pipetted by the pipette and wide-mouth pipette tip to mix, without shaking or vigorously pipetting. The product was stored at ~20° C. for use.

13) Sequencing by a Sequencer

The sequencing strategy is PE100+1.0+1.00.

The present inventors have established two sequencing libraries for the human derived standard DNA (NA12878) according to the steps as described above. The two sequencing libraries were tested on the sequencer via the PE100+10+100 strategy. The sequencing results are shown in Table 1.

TABLE 1

| | Read 1 AT separation rate | Read 1 GC separation rate | Read 2 AT separation rate | Read 2 GC separation rate |
|---|---|---|---|---|
| Library 1 | 0.41 | 0.35 | 0.35 | 0.36 |
| Library 2 | 0.38 | 0.35 | 0.37 | 0.41 |

It can be seen from the results in Table 1 that the base separation rates of the two sequencing libraries are low, both below 0.5%.

Comparative Example

In this comparative example, human derived standard DNA (NA12878) was subjected to DNA sequencing library construction followed by sequencing by the present inventors, in which the existing method for cyclizing a single-stranded nucleic acid molecule was adopted. The specific steps are as follows.

1) Sample Interruption

1 μg of genomic DNA in 80 μl of interruption reaction volume was interrupted into DNA fragments of 100 to 600 by (≈200 by of main band) by the Covaris E210.

The interruption parameters are below:

| | |
|---|---|
| Duty/cycle (0%) | 10 |
| Intensity | 5 |
| Cycle/burst | 200 |
| Time (s) | 60 |
| Cycle (s) | 5 |

2) Purification of Interrupted DNA

80 μl of the pretreated AMPure XP magnetic beads were transferred into a first PCR tube containing 80 μl of interrupted DNA obtained in step 1), which was gently pipetted by a pipette for 10 times to thoroughly mix, followed by incubation at room temperature for 5 minutes. Subsequently, the first PCR tube was stood on a magnetic stand and stilled for 2 minutes to allow the liquid to be clear. About 160 μl of supernatant in the first PCR tube was transferred into a second new PCR tube by the pipette while the first PCR tube was kept on the magnetic stand.

The second PCR tube was added with 40 μl AMPure XP magnetic beads, gently pipetted by the pipette for 10 times to thoroughly nix, and incubated at room temperature for 5 minutes. Subsequently, the second PCR tube was stood on the magnetic stand and stilled for 2 minutes to allow the liquid to be clear, after which the supernatant in this tube was discarded by the pipette while the tube was kept on the magnetic stand. 500 μl of freshly prepared 80% ethanol was added into each of the first and second PCR tubes for rinsing twice, after which 42 μl of TE buffer was added into each tube for DNA elution.

3) End Repair 50 ng of purified DNA fragments obtained in was transferred into a new PCR tube based on the concentration. Nuclease-free (NE) water was added to a total volume of 40 μl, and then 10 μl of DNA library end repair reaction solution for BGI platforms (BGISEQ500 and MGI2000) was added, which was reacted at 37° C. for 30 minutes. After that, the reactants were reacted at 65° C. for 15 minutes to deactivate the enzyme, followed by cooling to 4° C. at a rate of 0.1° C./second.

4) Addition of Adaptor

5 μl it of adaptor mixture (the adaptor containing at least 8 types of tags) and 25 μl of ligase reaction solution were added to the reactant solution in 3), followed by incubated at 23° C. for 1 hour and making up to a volume of 100 μl with water. Ampure XP beads in a usage amount of 0.5× (50 μl) were added for purification.

5) Purification of DNA Connected with Adaptor

Ampure XP beads in a usage amount of 0.5× (50 μl) were used for purification.

6) PCR Reaction

PCR reaction solution was added to the purified DNA connected with adaptor obtained in 5), with a total volume of 100 μl. The PCR reaction was performed on the PCR machine according to the procedure:

| | | |
|---|---|---|
| 95° C. | | 3 mins |
| 98° C. | 20 s | 6 cycles |
| 60° C. | 15 s | |
| 72° C. | 30 s | |
| 72° C. | | 5 mins |
| 4° C. | | holding |

7) Purification of PCR Product

After the completion of PCR reaction in 6), Ampure XP beads in a usage amount of 1× (100 μl) were used for purification of the PCR product.

8) Denaturation of PCR Product

Purified PCR product obtained in 7) was subjected to Qubit concentration detection. Subsequently, 330 ng of the PCR product was supplemented with TE buffer to 60 μl, and then 10 of original BGISEQ bridging nucleic acid molecule (10 μM) was added and mixed. The solution was placed on the PCR machine and incubated at 95° C. for 3 to 5 minutes to allow the double-stranded DNA molecules to be denatured into single-stranded nucleic acid molecules, immediately transferred into ice and stilled for 2 minutes. The original BGISEQ bridging nucleic acid molecule is adapted to form a first complementary region with the 5' terminal of the single-stranded nucleic acid molecule and form a second complementary region with the 3' terminal of the single-stranded nucleic acid molecule, in which the length of the first complementary region is equal to the length of the second complementary region.

9) Cyclization

A cyclization reaction mixture containing 12 μl ligation buffer, 1.2 μl ligation Enhancer, 0.4 μl T4 DNA ligase (NEB, 400 U/μl) and 36.4 μl NF water was formulated, which was added into 70 μl of the denatured DNA solution obtained in 8) and performed the cyclization reaction on the PCR machine according to the procedure of 37° C. for 60 mins and holding at 4° C.

10) Digestion

A digestion reaction mixture containing 0.8 μl 10× digestion buffer, 3.9 μl exonuclease I, 1.3 μl exonuclease HI and 2 μl NE water was formulated, which was added into 120 μl of cyclization reaction solution obtained in 9) and performed the digestion reaction on the PCR machine according to the procedure:

| | |
|---|---|
| 37° C. | 30 mins |
| 4° C. | holding |
| Addtion of 15 μl stop buffer to stop the digestion reaction | |

11) Purification of Digested Product

Ampure XP beads in a usage amount of 1.2× (170 μl) were used for purification of the digested product. The concentration of cyclized single-stranded nucleic acid molecules was detected by Qubit ssDNA Kit to be higher than 0.78 ng/μl. The product was stored at −20° C. for use.

12) DNB Preparation 6 ng of cyclized DNA library (i.e., cyclized single-stranded nucleic acid molecules) obtained in 11) was supplemented with water to 20 μl, followed by addition of 20 μl of DNA nanoball (DNB) preparation buffer, vortexed to mix, centrifuged briefly and reacted on the PCR machine according to the procedure of 9.5° C. for 1 min, 65° C. for 1 min, 40° C. for 1 min and holding at 4° C. After that, the PCR tube at 4° C. was taken out, 40 μl of DNB polymerase mixture I and 4 μl of DNB polymerase mixture II were added, vortexed to mix, centrifuged briefly and then reacted on the PCR machine according to the procedure of 30° C. for 20 nuns and holding at 4° C. After completion of the reaction, the PCR tube at 4° C. was transferred into an ice box and 20 μl of DNB stop buffer was added, which was gently pipetted by the pipette and wide-mouth pipette tip to mix, without shaking or vigorously pipetting. The product was stored at −20° C. for use.

13) Sequencing by a Sequencer

The sequencing strategy is PEI 00+10+100.

The present inventors have established two sequencing libraries for the human derived standard DNA (NA12878) according to the steps as described above. The two sequencing libraries were tested on the sequencer via the PE100+10+100 strategy. The sequencing results are shown in Table 2.

TABLE 2

| | Read1 AT separation rate | Read1 GC separation rate | Read2 AT separation rate | Read2 GC separation rate |
|---|---|---|---|---|
| Library 3 | 1.15 | 1.6 | 1.23 | 1.01 |
| Library 4 | 1 | 1.49 | 1.19 | 1.03 |

It can be seen from the results in Table 2 that the base separation rates of the two sequencing libraries are both above 1%.

Reference throughout this specification to "an embodiment", some embodiments", "one embodiment", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in an example", "in a specific example" or "in some examples" in various places throughout this specification are not necessarily referring to the same embodiment or example of the present disclosure. Further, the different embodiments or examples and the characteristics of the different embodiments or examples described in this specification may be combined by those skilled in the art without contradicting each other.

Although explanatory embodiments have been shown and described, it would be appreciated by those skilled in the art that the above embodiments cannot be construed to limit the present disclosure, and changes, alternatives and modifications can be made in the embodiments without departing from scope of the present disclosure.

What is claimed is:

1. A method for cyclizing a single-stranded nucleic acid molecule, comprising:

allowing a reaction mixture containing a splint nucleic acid molecule, a single-stranded nucleic acid molecule and a ligase to be under a condition suitable for ligation, so as to obtain a cyclized single-stranded nucleic acid molecule, wherein the splint nucleic acid molecule is for cyclizing the single-stranded nucleic acid molecule and consists of a 5' terminal fragment and a 3' terminal fragment, wherein the single-stranded nucleic acid molecule comprises:
  an insert fragment;
  a first adaptor, connected to a 5' terminal of the insert fragment; and
  a second adaptor, connected to a 3' terminal of the insert fragment, wherein the 5' terminal fragment of the splint nucleic acid molecule is adapted to form a first complementary region between the 5' terminal fragment of the splint nucleic acid molecule and at least a part of the first adaptor, and the 3' terminal fragment of the splint nucleic acid molecule is adapted to form a second complementary region between the 3' terminal fragment of the splint nucleic acid molecule and at least a part of the second adaptor, wherein the length of the first complementary region is equal to the length of the 5' terminal fragment of the splint nucleic acid molecule, and the length of the second complementary region is equal to the length of the 3' terminal fragment of the splint nucleic acid molecule, wherein the length of the first complementary region is different from the length of the second complementary region, and the method specifically comprises steps of:

(i) allowing the reaction mixture to be at a first temperature for a first predetermined time, wherein the first temperature is suitable to form the first complementary region;

(ii) allowing the reaction mixture obtained in step (i) to be at a second temperature for a second predetermined time, wherein the second temperature is suitable to form the second complementary region;

(iii) allowing the reaction mixture obtained in step (ii) to be at a third temperature for a third predetermined time, wherein the third temperature is suitable to unwind at least one of the first complementary region and the second complementary region;

(iv) subjecting the reaction mixture obtained in step (iii) to steps (i) and (ii) in sequence, and (v) subjecting the reaction mixture obtained in step (iv) to steps (iii), (i) and (ii) in sequence for at least one cycle, wherein the first temperature is higher than the second temperature.

2. The method according to claim 1, wherein the length of the first complementary region is at least 1.5 or at least 2 times longer than the length of the second complementary region; or the length of the first complementary region is at least 13 bp longer than the length of the second complementary region.

3. The method according to claim 2, wherein melting temperature (Tm) values of the first complementary region and the second complementary region differ by 10° C..

4. The method according to claim 1, wherein the 5' terminal fragment is of the nucleotide sequence of SEQ ID NO: 1, the 3' terminal fragment is of the nucleotide sequence of SEQ ID NO: 2, and the splint nucleic acid molecule is of the nucleotide sequence of SEQ ID NO: 3.

5. The method according to claim 1, wherein the first complementary region and the second complementary region each independently comprise 5 mismatched bases or fewer.

6. The method according to claim 1, wherein the insert fragment is derived from at least a part of a genomic fragment, and the genomic fragment is obtained by fragmenting and denaturing genomic DNA.

7. The method according to claim 1, wherein the difference between the second temperature and an optimal temperature of the ligase is 10° C. or below.

8. The method according to claim 1, wherein the second temperature is lower than an optimal temperature of the ligase, and the second temperature is 2 to 8° C. lower than the optimal temperature of the ligase.

9. The method according to claim 1, wherein the activity of the ligase at the second temperature is 50% or above of the highest activity.

10. The method according to claim 1, wherein the ligase is a thermostable ligase, and the thermostable ligase is capable of resisting a temperature of at least 50° C.

11. The method according to claim 10, wherein the thermostable ligase is Taq DNA ligase, and the optimal temperature of the ligase is 45° C.

12. The method according to claim 1, wherein
the first temperature is 35 to 65° C.,
the second temperature is 32 to 42° C., and
the third temperature is 94 to 98° C.

13. The method according to claim 1, wherein
the first temperature is 50° C.,
the second temperature is 37° C., and
the third temperature is 95° C.

14. The method according to claim 12, wherein the first predetermined time is 2 minutes,
the second predetermined time is 30 minutes, and
the third predetermined time is 30 seconds.

* * * * *